United States Patent [19]

Snyder et al.

[11] Patent Number: 4,593,095

[45] Date of Patent: Jun. 3, 1986

[54] XANTHINE DERIVATIVES

[75] Inventors: Solomon H. Snyder, Baltimore; John W. Daly, Bethesda, both of Md.; Robert F. Bruns, Ann Arbor, Mich.

[73] Assignee: The Johns Hopkins University, Baltimore, Md.

[21] Appl. No.: 467,894

[22] Filed: Feb. 18, 1983

[51] Int. Cl.$^4$ .................... C07D 239/36; A61K 31/52
[52] U.S. Cl. .................... 544/272; 514/263; 544/267
[58] Field of Search .................... 544/267; 424/253; 514/263

[56] References Cited

U.S. PATENT DOCUMENTS

| 2,840,559 | 6/1958 | Krantz et al. | 544/272 |
| 3,493,573 | 2/1970 | Joullie et al. | 544/272 |
| 4,299,832 | 11/1981 | Brown et al. | 544/272 |
| 4,452,788 | 6/1984 | Bristol et al. | 424/253 |

FOREIGN PATENT DOCUMENTS 982079  2/1965  United Kingdom.

OTHER PUBLICATIONS

Robert F. Bruns, Adenosine Antagonism by Purines, Pteridines and Benzopteridines in Human Fibroblasts, Biochemical Pharmacology, vol. 30, pp. 325–333, (1981).

*Primary Examiner*—Nicholas S. Rizzo
*Attorney, Agent, or Firm*—Cushman, Darby & Cushman

[57] ABSTRACT

Novel 8-phenylxanthines which are potent adenosine receptor antagonists.

5 Claims, No Drawings

XANTHINE DERIVATIVES

The invention described herein was made in the course of work under grant or award from the U.S. Department of Health and Human Services.

The present invention relates to certain novel 8-arylxanthines which are potent adenosine receptor antagonists or blockers.

Xanthines are well known drugs which are used clinically as bronchodilators, cardiotonics, diuretics and central nervous system stimulants. Available evidence indicates that the therapeutic actions of these drugs involves blockade or antagonism of adenosine receptors. However, many of the xanthines, such as theophylline (1,3-dimethylxanthine), have undesirable side-effects. Some of these side-effects may be due to actions at sites other than adenosine receptors. However, it is also likely that some side-effects are associated with blockade of the adenosine receptors themselves.

It appears that at least some of the side-effects caused by adenosine receptor antagonists could be avoided by the development of more potent blockers of such receptors which because of their increased blocking action, could be employed in lower doses and thus would be less likely to produce side-effects not associated with the adenosine receptor blockade. Additionally, where the therapeutic effect is due to blockade of one subtype of adenosine receptor while side-effects relate to blockade of a different subtype of adenosine receptor, drugs which are extremely potent at one receptor and substantially less active at another adenosine receptor should also have a reduced likelihood of side-effects.

The principal object of the present invention is to provide a novel group of xanthines which are highly potent as inhibitors or antagonists of adenosine receptors.

A more specific object of the invention is to provide a series of 8-arylxanthines, specifically 8-phenylxanthines, which are in general much more potent as adenosine receptor blockers than previously known xanthines.

Other objects will also be hereinafter apparent.

The novel 8-arylxanthines of the invention may be structurally described as compounds of Formula I

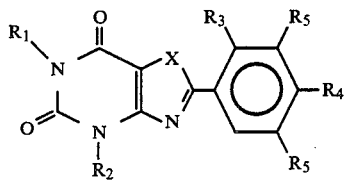

or the pharmaceutically-acceptable salts, esters, amides, glycosides or formaldehyde complexes thereof, wherein either (a):
X is NH, O or S;
$R_1$ is allyl, lower alkyl or cycloalkyl, the lower alkyl or cycloalkyl being optionally substituted with hydroxy, lower alkoxy or cyano;
$R_2$ is hydrogen, allyl, lower alkyl or cycloalkyl, the lower alkyl or cycloalkyl being optionally substituted as hereinafter described,
$R_3$ is $NH_2$ or OH;
$R_4$ is halogen, halo-lower alkyl (e.g. trifluoromethyl), phenyl, amino, hydroxy, carboxy, lower alkyl, cycloalkyl, lower alkoxy, cycloalkoxy, lower alkoxyamino, lower alkylamino or cycloalkylamino, the lower alkoxy, lower alkyl or cycloalkyl in each instance being optionally substituted with hydroxy, primary amino, secondary amino, tertiary amino or carboxy provided that $R_3$ and $R_4$ are not both amino when $R_1$ and $R_2$ are both methyl; and
$R_5$, which may be the same or different, are hydrogen, lower alkyl, lower alkoxy, halogen, hydroxy, nitro or amino; or (b)
X, $R_1$, $R_2$ and $R_5$ have the meanings stated in (a):
$R_3$ is hydrogen; and
$R_4$ is hydrogen or has the meaning stated in (a), except that $R_1$ is other than methyl or ethyl when $R_4$ is hydrogen, halogen, $C_1$–$C_3$ alkoxy, amino or alkylamino and $R_5$ is hydrogen or halogen.

The terms "alkyl", "lower alkyl", "alkoxy" or "lower alkoxy" as used above are intended to represent any alkyl or alkoxy of 1–6 carbon atoms, straight or branched, e.g., methyl, ethyl, propyl, isopropyl, butyl, isobutyl, pentyl or hexyl.

Any of the halogens are contemplated as $R_4$ and $R_5$ values. Thus, as an example, $R_4$ may be chloro, bromo or iodo and $R_5$ may be the same or different, e.g. fluoro or bromo although $R_5$ is preferably hydrogen.

Representative cycloalkyl substituents include cyclopropyl, cyclobutyl, cyclopentyl or cyclohexyl.

The optional substitution on the $R_2$ alkyl or cycloalkyl values may include hydroxy, methoxy, amino, methylamino, dimethylamino, carboxy, methylcarboxylate, ethylcarboxylate, carboxamide, dimethylcarboxamide, ureido, cyano and glycosyl. The glycosyl group may be attached to the alkyl chain by an ester, amide, ether, or glycosidic bond.

As indicated, pharmaceutically-acceptable salts, esters, amides and formaldehyde complexes of the indicated compounds, as well as the glycosides thereof, are contemplated. Typical salts include the alkali metal or alkaline earth metal salts although it is to be appreciated that other nontoxic salts are also intended. The xanthines where X is NH can form anions at alkaline pH (pK ~9) and thus can be advantageously administered as Na salts, choline salts, ethylenediamine complexes, etc. The 7-thiaxanthines and 7-oxoanthines do not form anions although many of the R substituent groups contemplated herein can form anions or cations. Hence a wide variety of suitable salts may be formed.

As noted in connection with the optional substitution referred to above for the $R_2$ substituent, the glycosides may be linked to the 3-position of the xanthine by glycosidic, amide or equivalent bond. On the other hand, complexes with formaldehyde (or other aldehyde) alone or with an amine may be formed through the 7-position nitrogen as shown by Formulas II and III:

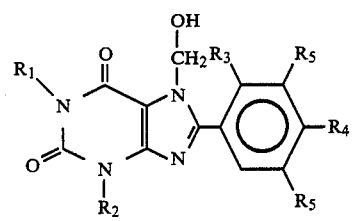

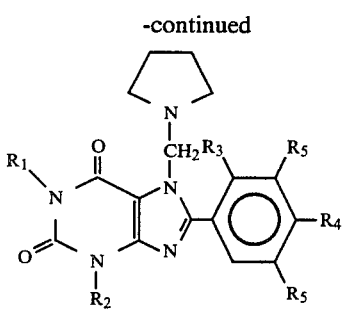

It is to be noted that the provisos included in the foregoing generic definition of the compounds of the invention (Formula I) are intended to exclude previously known 8-phenylxanthines or even some new compounds, which though new, demonstrate inferior potency as antagonists for adenosine receptors.

With respect to the compounds represented by Formula I, overall properties, such as water-solubility, blocking potency, etc., can be varied by appropriate selection of the $R_1$–$R_5$ substituents. For example, compounds where $R_1$ is methyl and $R_2$ is isobutyl, appear to be potent phosphodiesterase inhibitors.

The scope of permissible variation appears to be relatively narrow for the $R_1$ substituent. However, greater breadth of variation seems to be possible in the case of the $R_2$ substituent. Accordingly, the $R_2$ position may be used to carry substituents which are strongly hydrophilic in order to improve water-solubility without substantially affecting the potency of the resulting compound as an adenosine receptor antagonist.

The nature of the substitution in the $R_3$ and $R_4$ positions appears to be important for reasons of solubility and/or potency.

Specific examples of xanthines according to the invention include the following:

1,3-dipropyl-8-(2-amino-4-chlorophenyl)xanthine
1,3-dipropyl-8-(2,4-diaminophenyl)xanthine
1,3diethyl-8-(2-amino-4-chlorophenyl)xanthine
1,3-dipropyl-8-phenyl xanthine
1,3-dipropyl-8-(2-amino-4-chlorophenyl)-7-thiaxanthine
1,3-dipropyl-8-(2-amino-4-carboxyphenyl)xanthine
1,3-dipropyl-8-[2-amino-4-(carboxymethyl)phenyl]xanthine.

Of the above listed compounds, the first two (designated herein as B256 and B262 for convenience) demonstrate particularly outstanding activity as blockers of adenosine receptors.

A further particularly advantageous compound according to the invention is 1,3-diallyl-8-(2-amino-4-chlorophenyl)xanthine. This compound demonstrates useful activity as an adenosine receptor antagonist and is also useful as an intermediate or as a precursor to provide, for example, a tritium-labeled version of 1,3-dipropyl-8-(2-amino-4-chlorophenyl)xanthine.

There is a considerable amount of prior art relating to xanthines, including 8-phenylxanthines. As representative, it is noted that East German Pat. No. 31772 (Derwent 14969) of Oct. 31, 1961 describes various xanthines including, for example, 8-phenyltheophylline (i.e. 1,3-dimethyl-8-phenylxanthine) and processes for making the same. Belgium Pat. No. 616174 (Derwent 13790) of Oct. 15, 1964 and British Pat. No. 982,079 appear to be equivalent to the East German disclosure. These patents do not appear to describe the use of the compounds disclosed therein as adenosine receptor antagonists.

The following 8-phenylxanthines, among others, are believed to be known from the prior art using Formula I (where X is NH and $R_5$ is hydrogen) for ease of reference:

|      | $R_1$   | $R_2$   | $R_3$   | $R_4$ |
|------|---------|---------|---------|-------|
| (1)  | $CH_3$  | $CH_3$  | H       | H |
| (2)  | $CH_3$  | $CH_3$  | H       | $OCH_3$ or isopropoxy |
| (3)  | $CH_3$  | $CH_3$  | H       | $NO_2$ |
| (4)  | H       | $CH_3$  | H       | H |
| (5)  | $CH_3$  | H       | H       | H |
| (6)  | H       | H       | H       | H |
| (7)  | phenyl  | phenyl  | H       | H |
| (8)  | $CH_3$  | $CH_3$  | H       | $N(C_2H_5)_2$ |
| (9)  | $CH_3$  | $CH_3$  | H       | $N(CH_3)_2$ |
| (10) | $CH_3$  | $CH_3$  | Cl      | Cl |
| (11) | H       | $CH_3$  | H       | Cl |
| (12) | H       | $CH_3$  | H       | $OCH_3$ |
| (13) | $CH_3$  | $CH_3$  | H       | $CH_3$ |
| (14) | $CH_3$  | $CH_3$  | H       | F |
| (15) | $CH_3$  | $CH_3$  | H       | Cl |
| (16) | H       | H       | H       | Cl |
| (17) | H       | H       | H       | $OCH_3$ |
| (18) | $CH_3$  | $CH_3$  | H       | Br |
| (19) | H       | H       | H       | $NO_2$ |
| (20) | $C_2H_5$| $C_2H_5$| H       | H |
| (21) | $CH_3$  | $CH_3$  | COOH    | H |
| (22) | $CH_3$  | $CH_3$  | $NH_2$  | H |
| (23) | $CH_3$  | $CH_3$  | $NHCH_3$| H |
| (24) | $CH_3$  | $CH_3$  | $NO_2$  | H |

The above list is representative only and is not intended to include all previously disclosed 8-phenylxanthines. In any case, the compounds of the invention are distinguishable from the prior art compounds in respect of at least one of the substituents $R_1$–$R_5$ or combinations thereof.

It is to be noted that compound (1) listed above is 8-phenyltheophylline and compound (6) is 8-phenylxanthine. Elsewhere herein the symbols T and X are used to represent theophylline and xanthine, respectively.

The inhibiting effect of xanthines on adenosine receptors is referred to in a paper describing the binding of $N^6$-cyclohexyl[$^3$H]adenosine, and 1,3-diethyl-8-[$^3$H]phenylxanthine, also referred to as [$^3$H]CHA and [$^3$H]DPX, respectively, for convenience, to adenosine receptors in brain membrane (Bruns et al, Proc. Nat'l. Acad. Sci. USA, Vol. 77, No. 9, pp. 5547–5551, September 1980). This paper discloses, inter alia, the labeling of $A_1$ subtype of adenosine receptors in bovine brain membranes with [$^3$H]CHA and [$^3$H]DPX. The potencies of various xanthines in displacing [$^3$H]CHA from $A_1$ adenosine receptors in brain membranes, representing the inhibiting effect of these compounds on adenosine receptors measured as $IC_{50}$ nM values on a standard screen, are also shown. Theophylline, 8-phenyltheophylline and 8-(p-sulfophenyl)theophylline are included among the xanthines so evaluated.

A related paper by Bruns entitled "Adenosine Antagonism by Purines, Pteridines and Benzopteridines In Human Fibroblasts", Biochemical Pharmacology, Vol. 30, pp. 325–333 (1981) provides additional information regarding the potencies as adenosine antagonists of various xanthines (X) and theophyllines (T), including a number of 8-substituted theophyllines such as the 8-(p-chlorophenyl), 8-(p-bromophenyl)-, 8-(p-methoxyphenyl)-, 8-(p-nitrophenyl)-, 8-(p-dimethylaminophenyl)-, 8-(p-methylphenyl)-, 8-(3,4-dichlorophenyl)-, 8-(o-carboxyphenyl)- and 8-(2,6-dimethyl-4-hydroxyphenyl)-derivatives.

Another generally related paper by Snyder et al is entitled "Adenosine Receptors and Behavorial Actions of Methylxanthines", Proc. Nat'l. Acad. Sci. USA, Vol. 78, No. 5, pp. 3260–3264, May 1981.

The 8-phenylxanthines of the invention may be synthesized in any convenient fashion, e.g. according to the abovementioned East German No. 31772 or its equivalent Belgian Pat. No. 616,174 or British Pat. No. 982,079. In a preferred method, the appropriate 5,6-diaminouracil, itself prepared by reduction of the 5-nitroso-6-amino-uracil, is acylated to form the corresponding 5-acylamino-6-amino-uracil which is then ring-closed. Conventional acylating and ring-closing conditions may be used. For example, an appropriately substituted benzoic acid may be employed to form the 5-acylamino- compound. Ring closure may be effected by, for example, heating at the boil in 2.5N. NaOH for a sufficient period of time, e.g. 5 minutes, or by heating in $POCl_3$ for an appropriate time, e.g. 20 minutes or so.

The potency of the present compounds as adenosine receptor antagonists may be determined on the standard screen which involves blocking $N^6$-cyclohexyl [$^3$H]adenosine binding to adenosine receptors as described in the 1980 Bruns et al paper referred to above. Briefly, the screen, as used herein, involved the following:

10 mg. original tissue wet weight of bovine brain membranes were incubated for 2 hours at 25° C. with the test compound and 0.5 nM [$^3$H]CHA in 2 ml of 50 mM Tris.HCl pH 7.7. The test compound and [$^3$H]CHA were added to the tube first, and the incubation was initiated by addition of the tissue. Incubation was terminated and samples were collected on GF/B filters under vacuum, washed three times, and counted in a liquid scintillation counter. Dose-inhibition curves were generated with four to eight concentrations of the test compound in triplicate incubations. $IC_{50}$ values were computed from total binding (no compound), nonspecific binding (10 $\mu$M L-PIA), and the dose-inhibition data using a non-linear least-squares fit to a competitive inhibition model. $K_i$ values were calculated from the Cheng-Prusoff equation (Biochem. Pharmacol. 22, 3099–3108 (1973)). Compounds with $K_i$ values below 0.5 nM were tested in binding assays with only 2.5 mg wet weight of tissue in order to avoid conditions where the receptor concentration exceeded the $K_i$.

Tests of the present compounds in the foregoing screen indicate that the most active compound of the invention (B256) has an extraordinary adenosine receptor activity, with a $K_i$ for adenosine $A_1$ receptors of $2.2 \times 10^{-11}$ M when using bovine brain for test purposes. The compound accordingly appears to be approximately 4,000,000 times more potent than xanthine itself and 60,000 to 70,000 times more potent than theophylline.

In connection with the foregoing, it is noted that $A_1$ receptors from bovine brain have an unusually high affinity for 8-phenylxanthines, and bovine brain was chosen for test purposes for that reason, in order to ensure that even less potent analogs would have $IC_{50}$ values below their solubility limits. The more "normal" $A_1$ receptor in rat brain has a $K_i$ of 5 nM for compound B256, 150 nM for 8-phenyltheophylline, and 10 $\mu$M for theophylline. Thus, although both 8-phenylxanthines are much less potent in rat than in bovine brain, 1,3-dipropyl-8-(2-amino-4-chlorophenyl)xanthine (B256) is still about 30-fold more potent than 8-phenyltheophylline and 2000-fold more potent than theophylline using rat brain.

Theophylline is itself an adenosine antagonist which is used clinically as a bronchodilator in the treatment of asthma. The present compounds should also be useful in the same way as theophylline or other known xanthines, based on the indicated inhibition or blocking of adenosine receptors. This would include not only use as bronchodilators in the treatment of asthma but also use for cardiotonic effects in the treatment of heart failure, for diuretic effects in the treatment of high blood pressure or renal failure and for central nervous stimulant effects in treating depression. However, because of their surprisingly greater potency as adenosine receptor antagonists, the present compounds should be effective to block adenosine receptors in substantially lower amounts with consequent reduction in possible side effects.

It is contemplated that the present compounds would be used in the form of conventional pharmaceutical compositions with the usual types of carriers as in the case of the known xanthines or other adenosine receptor antagonists or blockers. It is also contemplated that these compositions, e.g. tablets or capsules for oral administration or sterile solutions for injection, would contain the usual amount of active component, e.g. from 0.01 to 0.5% by weight, based on the weight of the composition although, as noted, the dosages should be reduced to account for the generally greater activity of the present compounds.

The invention is illustrated, but not limited, by the following examples:

EXAMPLE 1

Synthesis of 1,3-Dipropyl-8-(2-Amino-4-Chlorophenyl)Xanthine (B256)

1,3-dipropyl-8-(2-amino-4-chlorophenyl)xanthine was synthesized by a modification of the method of Pfleiderer and Kempter (Ang Int. Ed. 6:259–260, 1967). 2-nitro-4-chlorobenzoic acid 0.02 mol) was dissolved in 30 ml of methanol. 1,3-dipropyl-5-nitroso-6-aminouracil (0.01 mol) was added with stirring, followed by 0.2 mol diisopropylcarbodiimide (DICD).

After ten minutes, the white precipitate, 1,3-dipropyl-5-[(2-nitro-4-chlorobenzoyl)oxy]imino-6-(2-nitro-4-chlorobenzoyl) iminouracil, was collected by filtration. To the dried intermediate was added 15 ml of 22% ammonium sulfide. After ten minutes, concentrated HCl was added to pH 8 in a hood and the precipitate was collected by filtration. The product was roughly a 50:50 mixture of 1,3-dipropyl-8-(2-amino-4-chlorophenyl)xanthine and 1,3-dipropyl-5-[(2-amino-4-chlorobenzoyl)amino]-6-aminouracil.

In order to complete the cyclization, the crude product was boiled in 2.5N KOH for 20 minutes, neutralized, and filtered. The product was purified once by dissolving in KOH and precipitating with HCl and again by recrystallizing from dimethylformamide. The product was identified by chemical ionization mass spectrometry and elemental analyses. Yield was 2.1%.

EXAMPLE 2

Synthesis of 1,3-Dipropyl-8-(2,4-Diaminophenyl) Xanthine (B262)

1,3-dipropyl-5,6-diaminouracil (0.01 mol) was suspended in 30 ml THF. N-trifluoroacetyl-4-nitroanthranilic acid-trifluroacetic acid mixed anhydride (0.01 mol) was added and the suspension was stirred at room temperature for 30 minutes, then evaporated in a rotary evaporator at 37° and then at 60°. The solid was boiled in 40 ml 2.5N KOH for five minutes, filtered hot, adjusted to pH 8.0 with concentrated HCl, filtered, and washed with H$_2$O. The precipitate was dissolved in 20 ml 2.5N KOH, heated, 5 ml 22% ammonium sulfide added, boiled for one minute, brought to pH 8 with concentrated HCl, filtered, and washed with H$_2$O. Yield 7.2%. Chemical ionization mass spectroscopy with NH$_3$ gave the M+1 peak at M/e 343. Microanalysis was consistent with 75% product and 25% thiol impurities. The product was not purified further because the thiols appeared to protect the desired product from oxidation.

EXAMPLE 3

Synthesis of 8-(2-Amino-4-Chlorophenyl) Theophylline (B246)

1,3-dimethyl-5,6-diaminouracil (0.01 mol) was suspended in 50 ml methanol. 2-amino-4-chlorobenzoic acid (0.01 mol) was added, followed by 0.01 mol of DICD. The reactants were stirred at room temperature for 15 min, then filtered and washed with methanol. The solid was boiled in 40 ml 2.5N NaOH for five min, filtered hot, and the eluate was left to cool for three hours. The material which precipitated on cooling was filtered without washing, redissolved in 40 ml water, and precipitated by neutralization with concentrated HCl. The solid was collected by filtration, washed with H$_2$O, and dried. The product was purified by suspending in 100 ml water, adding NaOH until the compound was dissolved, filtering, precipitating the solid with HCl, filtering, washing with H$_2$O, and drying. The product was identified by chemical ionization mass spectrometry and elemental analysis. Yield 12.5%.

EXAMPLE 4

Synthesis of 1,3-Dipropyl-8-Phenylxanthine (B255)

1,3-dipropyl-5,6-diaminouracil (0.01 mol) was dissolved in 30 ml methanol, followed by 0.01 mol of benzoic acid and then 0.01 mol of DICD. The solution was stirred for 30 min at room temperature, filtered, and washed with a small amount of methanol. The solid was boiled for ten minutes in 2.5N KOH, filtered hot, and the liquid neutralized with concentrated HCl. The solid was collected by filtration, washed with water, redissolved in 100 ml with a minimum amount of KOH, precipitated by neutralization with HCL, filtered, washed with water, and dried. The product was identified by chemical ionization mass spectrometry and elemental analysis. Yield 77%.

EXAMPLE 5

The following compounds are also representative of the invention and may be prepared in generally the same way as shown in the preceding examples:

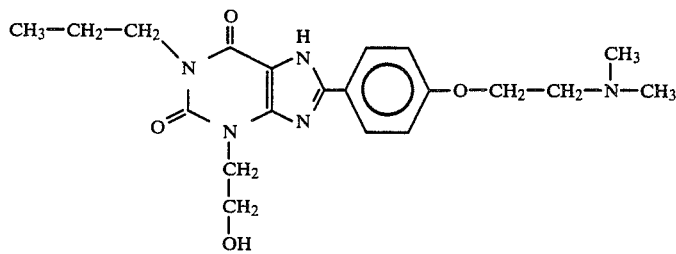

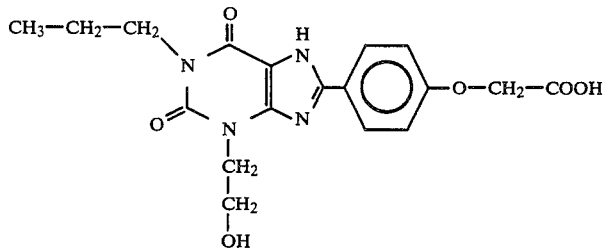

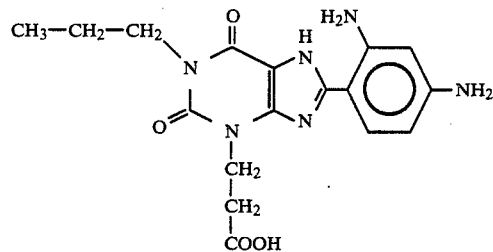

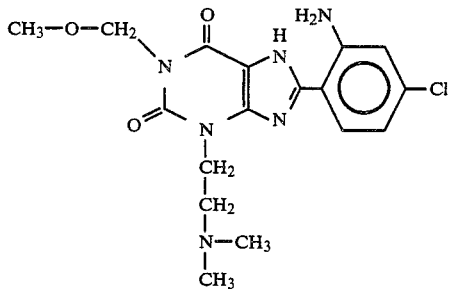

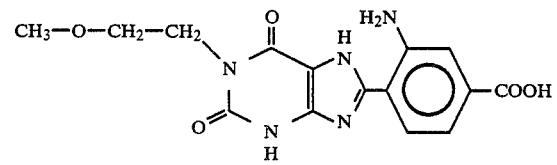

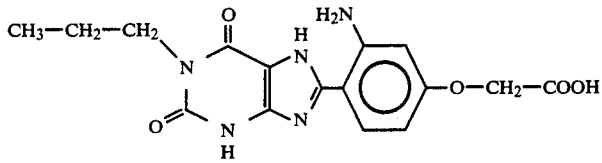

As indicated earlier, the potency of xanthines or other compounds as inhibitors of adenosine receptors can be determined by testing the compounds in the known screen referred to above and involving the use of [$^3$H]CHA in bovine brain membrane. The activities of the compounds of Examples 1 to 4 are compared below in Table I with other structurally related compounds, at least some of which (xanthine, B7, B80, B52, B87 and B70) are known compounds, in terms of IC$_{50}$ (nM) values determined by screening the compounds against $^3$H]-cyclohexyladenosine in bovine brain:

TABLE I

| | | IC$_{50}$ (nM) |
|---|---|---|
| | xanthine | 200,000 |
| B7 | theophylline (1,3-dimethylxanthine) | 3,000 |
| B80 | 1,3-dipropylxanthine | 200 |
| B52 | 8-phenyltheophylline | 3 |
| B87 | 8-(o-aminophenyl)theophylline | 5 |
| B70 | 8-(p-chlorophenyl)theophylline | 0.8 |
| B211 | 8-(p-aminophenyl)theophylline | 1.7 |
| B232 | 8-(2,4-diaminophenyl)theophylline | 8 |
| B246 | 8-(2-amino-4-chlorophenyl)theophylline | 0.15 |
| B255 | 1,3-dipropyl-8-phenylxanthine | 0.3 |
| B256 | 1,3-dipropyl-8-(2-amino-4-chlorophenyl)xanthine | 0.05 |
| B262 | 1,3-dipropyl-8-(2,4-diaminophenyl)xanthine | 0.2 |

It will be noted that the compounds of Examples 1 to 4 (Compounds B256, 262, 246 and 255, respectively) demonstrate IC50 (nM) values which are significantly lower (indicative of greater potency as adenosine receptor blockers or inhibitors) than those obtained with the other listed compounds. Particularly active is B256 (Example 1) whose activity is some 16 times greater than that of the most active prior art compound (B70). It is also noted that the inhibiting activity of the compound of Example 2 (B262) is four-fold greater than that of B70.

While B256 is extremely potent, it is hydrophobic and very water-insoluble. In certain cases, therefore, there may be an advantage in incorporating water solubilizing groups in the compound, e.g. in the 3-position (R$_2$). The compound B262, while substantially less active than B256, has much greater water-solubility and offers this as an advantage over B256 in cases where such solubility is important.

The results set forth in Table I indicate that the best results are obtained when R$_3$ and R$_4$ in Formula I (i.e., the ortho and para positions of the 8-phenyl substituent) are both substituted, particularly with amino as R$_3$ and chloro or other halogen as R$_4$, R$_5$ being hydrogen in both instances and R$_1$ and R$_2$ being lower alkyl. Increasing the length of the alkyl for R$_1$ and R$_2$ appears to improve the potency of the xanthines as inhibitors for adenosine receptors. Compare in this respect the results obtained with xanthine itself; theophylline (B7); and 1,3-dipropylxanthine. It is a particularly surprising aspect of the invention that while 8-phenyltheophylline is about 1000 times more potent than theophylline and 1,3-dipropyl substituents enhance the potency of theophylline by almost twenty times, the combination of 1,3-propyl substituents and the 8-phenyl substituent gives a synergistic effect such that 1,3-dipropyl-8-phenylxanthine is about 10,000 times more potent than theophylline. Accordingly, it is preferred for present purposes that R$_1$ and R$_2$ be the same or different alkyl with at least 3 carbon atoms.

The substantial potency of the compounds of the present invention is also evident from a comparison of the activities of such compounds with other compounds as determined versus [$^3$H-CHA] in bovine brain:

TABLE II

| | IC$_{50}$ (nM) |
|---|---|
| xanthine (X) | 200,000 |
| 3-methylX | 150,000 |
| 1-methylX | 6,000 |
| 1,7-dimethylX | 30,000 |
| 8-nitroT | 3,500 |
| caffeine | 20,000 |
| 7-(2-chloroethyl)T | 5,000 |
| 7-(2-hydroxyethyl)T | 100,000 |
| 7-(2,3-dihydroxypropyl)T | 800,000 |
| 1,3-diethylX | 3,000 |
| 8-(n-propyl)T | 100 |
| 8-cyclopentylT | 2 |
| 8-(p-methoxyphenyl)T | 1.5 |
| 8-(o-nitrophenyl)T | 80 |
| 8-(p-nitrophenyl)T | 8 |
| 8-(2,6-dimethyl-4-hydroxyphenyl)T | 30 |
| 8-(1-naphthyl)T | 80 |
| 8-(3-indolyl)T | 18 |
| 8-(p-bromophenyl)T | 0.8 |
| 8-(p-dimethylaminophenyl)T | 1.8 |
| 8-(p-methylphenyl)T | 0.8 |
| 8-benzylT | 1,500 |
| 8-cyclohexylT | 3 |
| 1,3-diallylX | 4,000 |
| 1-methyl-8-phenylX | 2.5 |
| 8-(3,4-dichlorophenyl)T | 5 |
| 8-(m-methoxyphenyl)T | 20 |
| 8-(m-nitrophenyl)T | 50 |
| 8-(m-dimethylaminophenyl)T | 80 |
| 8-(m-methylphenyl)T | 13 |
| 8-(p-hydroxyphenyl)T | 2 |
| 8-(p-ethoxyphenyl)T | 2 |
| 8-(2-pyridyl)T | 100 |
| 8-(3-pyridyl)T | 50 |
| 8-(4-pyridyl)T | 35 |
| 8-(2-furyl)T | 18 |
| 8-(o-carboxyphenyl)T | 2,500 |
| adenine | 800,000 |
| 1-ethyl-3-propyl-7-thiaxanthine | 8,000 |
| 8-methyladenine | 35,000 |
| alloxazine | 1,500 |
| 1,3-dimethylalloxazine | 25,000 |
| 8-(p-fluorophenyl)T | 3.5 |
| 8-(p-iodophenyl)T | 1.3 |
| 8-(3,4-dimethoxyphenyl)T | 20 |
| 8-(p-isopropylphenyl)T | 2.5 |
| 8-(2-thienyl)T | 5 |
| 8-(m-bromophenyl)T | 10 |
| 8-(m-hydroxyphenyl)T | 6 |
| 8-(m-aminophenyl)T | 10 |
| 8-(p-sulfophenyl)T | 500 |
| 8-(p-ethylphenyl)T | 0.8 |
| 8-(p-phenylphenyl)T | 3.5 |
| 8-(3,5-dimethoxyphenyl)T | 500 |
| 8-(2-naphthyl)T | 5 |
| 8-(m-fluorophenyl)T | 4 |

TABLE II-continued

| | IC$_{50}$ (nM) |
|---|---|
| 1,3-diethyl-8-phenylX | 2.5 |
| 1,3-diethyl-8-(p-bromophenyl)X | 1.0 |
| 8-(o-fluorophenyl)T | 12 |
| 8-(o-hydroxyphenyl)T | 10 |
| 8-(o-methoxyphenyl)T | 350 |
| 8-(o-methylphenyl)T | 6 |
| 8-(m-carboxyphenyl)T | 1,000 |
| 8-(p-carboxyphenyl)T | 50 |
| 8-(2,4-dimethoxyphenyl)T | 200 |
| 8-(2-amino-4-nitrophenyl)T | 2.5 |
| 8-(3-furyl)T | 4 |
| 8-ferrocenylT | 20 |
| 8-(5-bromo-2-furyl)T | 50 |
| 8-(N—methyl-2-pyrrolyl)T | 20 |
| 8-cyclopentylmethylT | 30 |
| 1-allyl-3-methyl-8-phenylX | 4 |
| 1-allyl-3-methyl-8-(2-amino-4-chlorophenyl)X | 2 |
| 8-(p-butoxyphenyl)T | 4 |
| 1,3-diethyl-8-(2-amino-4-chlorophenyl)X | 0.8 |
| 1,3-diallyl-8-(2-amino-4-chlorophenyl)X | 0.8 |
| 1-allyl-3-methyl-8-(2-amino-4-methylphenyl)X | 7 |
| 8-(2-amino-4-methylphenyl)T | 10 |
| 8-(5-methyl-2-thienyl)T | 5 |
| 8-(p-methylthiophenyl)T | 2 |

As noted, the most potent compounds of the invention appear to be those of Formula I which include propyl substituents for $R_1$ and $R_2$ in combination with the 8-phenyl, whether the latter is substituted or not. However, potent compounds are also obtained when $R_1$ and/or $R_2$ are other than propyl (or higher alkyl), provided the 8-phenyl group is substituted, preferably but not necessarily with at least two substituents in the 8-phenyl group, and most preferably with at least one such substituent in the para position.

Studies with various substituents on the 8-phenyl ring of 8-phenyltheophylline further indicate that the nature and positioning of such substituents can have a marked effect on the receptor affinity or blocking activity of the resulting compound. In general, these studies indicate that ortho substituents on the 8-phenyl ring generally reduce the receptor affinity of 8-phenyltheophylline, probably because the ortho substituent creates steric hindrance with the N-7 and N-9 of the xanthine. In agreement with this is the finding that ortho substitution with the more bulky methoxy and nitro groups causes the largest decrements in affinity. This suggests that the receptor prefers the 8-phenyl ring to be in the same plane as the xanthine ring. Of the various ortho substituents, the ortho amino causes the least reduction in potency of 8-phenyltheophylline, perhaps because it hydrogen bonds to the N-7 of the xanthine, stabilizing a conformation with the 8-phenyl and xanthine rings in the same plane.

Meta substituents generally reduce potency of 8-phenyltheophylline 3–100 fold. The 8-phenyl ring has two possible meta positions ($R^5$) and the ring rotates freely. If only one of the meta positions was important for receptor interactions, then even unfavorable substituents would reduce potency only about two-fold, since the rotamer with the unsubstituted meta position in contact with the receptor and the substituted meta in the "unimportant" position would still have full affinity. The far greater reductions in potency observed with meta substituents suggest that both meta positions are important.

Para substituents can either increase or decrease the potency of 8-phenyltheophylline. Except for the p-carboxyl group, the changes in potency are not large, being less than four-fold in all cases. Hydrogen bonding to the receptor does not appear crucial since an amino group, which can be both a donor and acceptor of hydrogen bonds, and a chloro, which is neither a donor nor an acceptor of such bonds, have similar effects. Development of a resonance structure with a substituent does not appear to be crucial since a methyl group, which does not provide a resonance form, considerably enhances potency. Donation or withdrawal of electrons from the 8-phenyl ring does not appear of importance, since both electron donating and withdrawing groups have similar effects. Accordingly, it is most likely that optimal activity in this position is associated largely with steric factors.

Though para substituents on the 8-phenyl ring produces very potent agents, disubstitution of the 8-phenyl ring in the ortho and para positions ($R_3$ and $R_4$) clearly give the compounds of maximum potency, particularly when $R_1$ and $R_2$ are longer chain alkyl than methyl or ethyl. An ortho amino group adds hydrophilicity and although this group added alone to 8-phenyltheophylline lowers affinity in [$^3$H]CHA binding slightly, it increases affinity three-fold or so when added to 8-(p-chlorophenyl)-theophylline. This apparently synergistic interaction suggests that one group (probably the o-amino) stabilizes a conformation which is favorable to the binding of the other group.

The following additional data shows adenosine receptor affinities of various xanthines in terms of inhibition of [$^3$H]CHA binding to $A_1$ adenosine receptors in bovine brain membranes using the method described earlier herein.

TABLE III

| Substituents | Inhibition of [$^3$H]CHA Binding $K_i$, nM |
|---|---|
| None (xanthine) | 99,000 |
| 1-Methyl | 2,600 |
| 1,7-Dimethyl | 7,400 |
| 1,3-Dimethyl (theophylline) | 1,600 |
| 3,7-Dimethyl (theobromine) | 68.000 |
| 1,3,7-Trimethyl (caffeine) | 11,000 |
| 1,3-Diethyl | 1,400 |
| 1,3-Dipropyl | 100 |
| 1,3-Dimethyl-8-phenyl | 1.2 |
| 1,3-Diethyl-8-phenyl (DPX) | 2.0 |
| 1,3-Dipropyl-8-phenyl | 0.12 |

The last compound in Table III is the only one listed in the table which is representative of the invention. This compound, which corresponds to Formula I when $R_1$ and $R_2$ are propyl, X is NH and $R_3$, $R_4$ and $R_5$ are all hydrogen, is clearly much more potent as an inhibitor than other compounds.

The data set out below in Table IV shows the adenosine receptor affinity of various 8-phenyltheophyllines with the indicated substituents on the 8-phenyl ring:

TABLE IV

| | Inhibition of [$^3$H]CHA Binding ($K_i$, nM) | | |
|---|---|---|---|
| | Substituent on 8-Phenyl Ring at | | |
| Substituent | ortho | meta | para |
| H | 1.2 | 1.2 | 1.2 |
| Bromo | — | 4.0 | 0.34 |
| Methyl | 3.6 | 5.4 | 0.51 |
| Methoxy | 190 | 8.7 | 0.63 |
| Chloro | — | — | 0.64 |
| Amino | 2.3 | 5.8 | 0.69 |
| Fluoro | 6.8 | 2.4 | 1.8 |
| Hydroxy | 4.8 | 3.1 | 2.0 |
| Nitro | 49 | 22 | 4.0 |

TABLE IV-continued

| | Inhibition of [³H]CHA Binding ($K_i$, nM) | | |
|---|---|---|---|
| | Substituent on 8-Phenyl Ring at | | |
| Substituent | ortho | meta | para |
| Carboxyl | 21,000 | 540 | 18 |

Table V shows the effects of disubstitution on the 8-phenyl ring of 8-phenyltheophylline with respect to adenosine receptor affinity as determined by inhibition of [³H]CHA binding to $A_1$ adenosine receptors in bovine brain membrances.

TABLE V

| 8-Phenyl Substituents | Xanthine Substituents | Inhibition of [³H]CHA binding $K_i$, nM |
|---|---|---|
| H | 1,3-Dimethyl | 1.2 |
| 2-Amino-4-nitro | 1,3-Dimethyl | 1.2 |
| 2,4-Diamino | 1,3-Dimethyl | 5.9 |
| 2-Amino-4-chloro | 1,3-Dimethyl | 0.20 |
| H | 1,3-Diethyl | 2.0 |
| 2-Amino-4-chloro | 1,3-Diethyl | 0.32 |
| H | 1,3-Dipropyl | 0.12 |
| 2,4-Diamino | 1,3-Dipropyl | 0.14 |
| 2-Amino-4-chloro | 1,3-Dipropyl | 0.022 |

The following methods were employed in the preparation of various intermediates or final xanthine products referred to in the foregoing examples or in Tables I–V:

1,3-Dialkyl-5-nitroso-6-aminouracils.

The 1,3-disubstituted 6-aminouracil was suspended (0.5M) with vigorous stirring in water with one equivalent of sodium nitrite. Concentrated HCl was added in small amounts to maintain the pH at 4.0. When the pH stopped rising, HCl was added to pH 2.5 and the thick precipitate was filtered. The product was dried and used without further characterization.

1,3-Dialkyl-5,6-diaminouracils:

Sodium Hydrosulfite Method 1,3-Diethyl-5,6-diaminouracil and 3-allyl-1-ethyl-5,6-diaminouracil were prepared by reduction of the corresponding 5-nitroso compounds with sodium hydrosulfite. The nitroso compound was suspended in water (1M) and sodium hydrosulfite was added until the nitroso color disappeared. An additional quantity of sodium hydrosulfite was added and the solution was left at 4° C. overnight. The precipitated bisulfite salt of the product was collected by filtration.

1,3-Dialkyl-5,6-diaminouracils

Ammonium Sulfide Method

To 0.01 mol of 1,3-dipropyl-5-nitroso-6-aminouracil or 1,3-diallyl-5-nitroso-6-aminouracil was added 10 ml of 22% light ammonium sulfide in a fume hood. After about 2 minutes, the suspension became hot and in some cases boiled violently. After 30 minutes, the ammonium sulfide was removed in a rotary evaporator. The solid remaining had a strong sulfide stench but gave a satisfactory coupling reaction with benzoic acid.

1,3-Dialkyl-5-acylamino-6-aminouracils

Method A

Fusion with the Carboxylic Acid 1,3-dimethyl-5,6-diaminouracil and the appropriate carboxylic acid were heated above their mixed melting point (120–180° C.) until solid or until three hours had elapsed, whichever came first.

1,3-Dialkyl-5-acylamino-6-aminouracils

Method B

Fusion with the Acyl Chloride 1,3-dimethyl-5,6-diaminouracil was suspended in an excess of the appropriate acid chloride and heated to 120–160° C. for 30 minutes to 2 hours.

1,3-Dialkyl-5-acylamino-6-aminouracils

Method C

EDAC in Water 1,3-dimethyl-5,6-diaminouracil was dissolved at 0.3M boiling water and allowed to cool below 40° C. One equivalent of the appropriate carboxylic acid was added and the pH was raised slowly with NaOH until the carboxylic acid was dissolved (pH 4 to 7). One equivalent of EDAC was added with stirring and the pH was kept constant by addition of HCl. When the pH stopped rising, the precipitated amide was collected by filtration. In the case of 1,3-dimethyl-5-(p-sulfobenzoylamino)-6-aminouracil, the product was precipitated by addition of MeOH.

1,3-Dialkyl-5-acylamino-6-aminouracils

Method D

DICD in Methanol

The 1,3-dialkyl-5,6-diaminouracil (free base or bisulfite salt) and the appropriate carboxylic acid were dissolved or suspended at 0.3 M each in MeOH. One equivalent of DICD was added and the copious amide precipitate was collected by filtration after 5 to 30 minutes. In a few cases (e.g., 1,3-diethyl-5,6-diaminouracil with 2-amino-4-chlorobenzoic acid) the amide was soluble in MeOH and had to be collected by precipitation with water or evaporation of the MeOH.

1,3-Dialkyl-5-acylamino-6-aminouracils

Method E

EDAC in Methanol

This method is the same as Method D, except that EDAC was used in place of DICD.

1,3-Dialkyl-5-acylamino-6-aminouracils

Method F

Mixed Anhydride

To 2-amino-4-nitrobenzoic acid in a small volume of THF was added two equivalents of trifluoroacetic anhydride. After 10 minutes, trifluoroacetic acid and its anhydride were removed in a rotary evaporator. The product 2-trifluoroacetamido-4-nitrobenzoic acid-trifluoroacetic acid mixed anhydride (0.01 mol) was reacted with 1,3-dialkyl-5,6-diaminouracil (0.01 mol) in THF for 60 minutes. In the case of the 1,3-dimethyl derivative, the product 1,3-dimethyl-5-(2-trifluoroacetamido-4-nitrobenzamido)-6-aminouracil precipitated in 140 ml THF and was collected by filtration. The 1,3-dipropyl homolog was soluble in 30 ml THF and was collected in a rotary evaporator. When the corresponding xanthines were produced by ring closure in 2.5N KOH (see below), the trifluoroacetyl group was lost.

8-Substituted Xanthines

Ring Closure in NaOH

The 1,3-dialkyl-5-acylamino-6-aminouracil (0.3 M) was boiled for 5 to 20 minutes in 2.5N NaOH (or KOH). Uracils which were insoluble or had electron-donating groups on the acyl moiety required the longest times.

Isolation of 8-Substituted Xanthines

When possible, the xanthine in boiling NaOH was filtered to remove impurities which were insoluble in boiling NaOH. Xanthines which were synthesized by Method A usually contained an alkali-insoluble material of molecular weight 252. This step was omitted when the xanthine was insoluble in boiling NaOH or when there was precipitation during filtration. The solution of xanthine in NaOH was cooled to 0°. If the xanthine precipitated as the sodium salt, it was collected by filtration without washing, redissolved in distilled water, precipitated by neutralization (pH 7 to 9) with concentrated HCl, filtered, and washed with water. If the xanthine remained dissolved at 0° in 2.5N NaOH, it was neutralized, filtered and washed. The final wash was omitted for 8-(p-sulfophenyl)theophylline, which precipitated as the sodium salt. For the 8-(carboxyphenyl) theophyllines, HCl was added to pH 6 in the precipitation step.

8-(o-Hydroxyphenyl)theophylline

Ring Closure in POCl$_2$ 8-(o-hydroxyphenyltheophylline could not be prepared by the usual NaOH ring closure, even when 1,3-dimethyl-5-(acetylsalicyloyl)amino-6-aminouracil was used as intermediate. Instead, 1,3-dimethyl-5-(acetylsalicyloyl)amino-6-aminouracil was refluxed for 10 minutes in POCl$_2$. The cooled POCL$_2$ solution was added slowly to a large volume of ice cold water with vigorous stirring. After the POCl$_2$ was completely hydrolyzed, the solution was neutralized with KOH pellets and filtered. The filtrate was a mixture of the xanthine and the uncycled amide. The latter was eliminated by boiling for 5 minutes in 2.5N KOH and the xanthine was collected by neutralization and filtration.

1,3-Dipropyl-8-(2,4-diaminophenyl)xanthine

Reduction of Nitro Derivative

Method G 1,3-dipropyl-8-(2-amino-4-nitrophenyl)xanthine (0.007 mol) was dissolved in 20 ml boiling 2.5N KOH. Five ml of 22% ammonium sulfide was added, and the solution was removed from heat after 1 minute. HCl was added to pH 8 in a hood, and the product was collected by filtration and washed with water. About 25% of the product was a sulfur-containing impurity. Since this impurity appeared to protect the xanthine from oxidation, no attempt was made to further purify the xanthine. 8-(2,4-diaminophenyl)theophylline was synthesized in the same way.

1,3-Dialkyl-8-(2-amino-4-chlorophenyl)xanthine

From Acylated Nitrosouracil

Method H 1,3-dipropyl-8-(2-amino-4-chlorophenyl)xanthine and 1,3-diallyl-8-(2-amino-4-chloropheny)xanthine were synthesized by the method of Pfleiderer and Kempter. 2-nitro-4-chlorobenzoic acid (0.02 mol) was dissolved in 30 ml of MeOH. 1,3-dialkyl-5-nitroso-6-aminouracil (0.1 mol) was added with stirring, followed by 0.02 mol DICD. After 10 minutes, the white precipitate, 1,3-dialkyl-5-[2-nitro-4-chlorobenzoyl) oxy]imino-6-(2-nitro-4-chlorobenzoyl)iminouracil, was collected by filtration. To the dried intermediate was added 15 ml of 22% ammonium sulfide. After 10 minutes, concentrated HCl was added to pH 8 in a hood and the precipitate was collected by filtration. The product was roughly a 50:50 mixture of 1,3-dialkyl-8-(2-amino-2-chlorophenyl)xanthine and 1,3-dialkyl-5-[2-amino-4-chlorobenzoyl)amino]-6-aminouracil. In order to complete the cyclization, the crude product was boiled in 2.5N KOH for 20 minutes, neutralized, and filtered.

Product Purification

When microanalysis for a xanthine did not agree with theoretical values, the xanthine was suspended at 0.1 M in water and dissolved with a minimal amount of KOH. After filtration, the xanthine was neutralized, collected by filtration, and washed with water. If microanalysis was still incorrect, the compound was recrystallized from dimethylformamide.

Characterization of Products

All products gave correct parent ions (M+1) on NH$_3$ chemical ionization spectrometry. Except for the carboxyphenyltheophyllines, M+18 peaks were not seen. This allowed easy detection of the M+19 uncyclized amide. The structure of 8-p-sulfophenyltheophylline was confirmed by proton magnetic resonance in deuterated DMSO. Compounds were dried before elemental analysis. Most compounds were purified until satisfactory microanalyses were achieved, but a few had to be used without purification because of the small amount of material available.

Solubility of 8-Phenylxanthines

ALL of the uncharged 8-phenylxanthines were quite insoluble in water. 8-phenyltheophylline was soluble at 10 μM in water, and 1,3-diethyl-8-phenylxanthine was soluble at 3 μM. The more hydrophobic analogs appeared to be considerably less soluble in water. 8-phenyltheophylline was soluble at 1 mM in DMF and in 0.01N NaOH, but was almost insoluble in ethanol. More hydrophobic analogs were less soluble in NaOH but more soluble in DMF. Unlike most 8-phenylxanthines, 1,3-dipropyl-8-(2-amino-4-chlorophenyl)xanthine was soluble at 1 mM in ethanol. It was soluble at 30 mM in DMF and at 1 mM in hot 0.1N KOH.

Stock solutions of the 8-phenylxanthines were made up in 0.1N KOH or DMF and stored at 4° C. pending their testing. KOH solutions were stable for about 3 weeks and DMF solutions were stable longer. KOH solutions sometimes precipitated irreversibly if frozen. Dilutions were made up fresh from stock. Solutions were diluted directly to 1 μM or 10 μM in distilled water and (if possible) immediately diluted further.

In summary, the compounds of Formula I, particularly those where X is NH, and R$_1$ and R$_2$ are lower alkyl of at least 3 carbons, R$_3$ is NH$_2$, R$_4$ is halogen, particularly chlorine, and R$_5$ is hydrogen, are extremely potent adenosine receptor antagonists and they should be useful as, for example, bronchodilators, cardionics, diuretics, and central nervous system stimulants. In addition, when labelled with tritium, iodine-125, or some other radiolabel, the present compounds may be used as radioligands for binding to adenosine receptors. Such a radioligand may be used for measurement of adenosine receptor levels or for measurement of levels of adenosine or adenosine analogs. Such measurements are useful as research tools and as diagnostic tests.

It is also contemplated that at least some of the present compounds will be potent inhibitors of cyclic GMP phosphodiesterase.

The invention described herein was made in the course of work under a grant or award from the Department of Health and Human Services.

The scope of the invention is defined in the following claims wherein.

We claim:

1. A compound, which in its free base form, has the formula

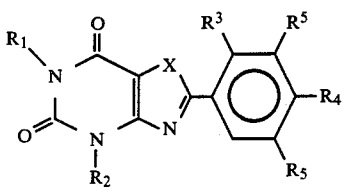

wherein

X is NH;

$R_1$ is allyl, alkyl of 2–6 carbons, or cycloalkyl of 3 to 6 carbons, the lower alkyl or cycloalkyl being optionally substituted with hydroxy, lower alkoxy or cyano;

$R_2$ is hydrogen, allyl, lower alkyl or cycloalkyl, the lower alkyl or cycloalkyl being optionally substituted as hereinafter described, $R_3$ is $NH_2$ or OH;

$R_4$ is halogen, halo-lower alkyl, phenyl, amino, carboxy, lower alkyl, cycloalkyl, lower alkoxy, cycloalkoxy, lower alkoxy amino, lower alkyl amino or cycloalkylamino, the lower alkoxy, lower alkyl or cycloalkyl in each instance being optionally substituted with hydroxy, amino, methylamino, dimethylamino or carboxy; and $R_5$, which may be the same or different, are hydrogen, lower alkyl, lower alkoxy, halogen, hydroxy, nitro or amino.

2. A compound according to claim 1 wherein X is NH, $R_1$ and $R_2$ are alkyl of 3 or more carbons, $R_3$ is amino, $R_4$ is halogen and $R_5$ is hydrogen.

3. A compound according to claim 1 wherein $R_1$ and $R_2$ are alkyl of at least 3 carbons.

4. A compound according to claim 3 wherein $R_1$ and $R_2$ are both propyl.

5. A compound according to claim 1 which is 1,3-dipropyl-8-(2-amino-4-chlorophenyl)xanthine.

* * * * *